(12) United States Patent
Le Grand et al.

(10) Patent No.: US 9,980,970 B2
(45) Date of Patent: May 29, 2018

(54) USE OF PAR-1 ANTAGONISTS FOR PREVENTING AND/OR TREATING PELVI-PERINEAL FUNCTIONAL PATHOLOGICAL CONDITIONS

(71) Applicant: PIERRE FABRE MEDICAMENT, Boulogne-Billancourt (FR)

(72) Inventors: Bruno Le Grand, Teyssode (FR); Didier Junquero, Castres (FR); Nicolas Monjotin, Castres (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days. days.

(21) Appl. No.: 15/101,170

(22) PCT Filed: Oct. 31, 2014

(86) PCT No.: PCT/EP2014/073453
§ 371 (c)(1),
(2) Date: Jun. 2, 2016

(87) PCT Pub. No.: WO2015/090705
PCT Pub. Date: Jun. 25, 2015

(65) Prior Publication Data
US 2016/0287603 A1    Oct. 6, 2016

(30) Foreign Application Priority Data
Dec. 16, 2013  (FR) ..................... 13 62682

(51) Int. Cl.
*A61K 31/5377*  (2006.01)
*A61K 31/495*   (2006.01)
*A61K 31/443*   (2006.01)

(52) U.S. Cl.
CPC ........ *A61K 31/5377* (2013.01); *A61K 31/443* (2013.01); *A61K 31/495* (2013.01)

(58) Field of Classification Search
CPC .............. A61K 31/5377; A61K 31/443; A61K 31/495; C07D 241/02
See application file for complete search history.

(56) References Cited

U.S. PATENT DOCUMENTS 8,217,046 B2 * 7/2012 Perez ................. C07D 295/185
514/255.01

FOREIGN PATENT DOCUMENTS

| FR | 2902426 A1 | 12/2007 |
| WO | WO 03/089428 A1 | 10/2003 |
| WO | WO 2007/147824 A1 | 12/2007 |

OTHER PUBLICATIONS

Saban et al (BMC Physiology, 2007, 7:4, 1-15).*
Moffatt (Naunyn-Schmiedeberg's Arch Pharmacol, 2007, 375:1-9).*
Chatterjee et al (J.Thromb.Thrombolysis, 2013, 35:1-9).*
Ahn et al., "Inhibition of Cellular Action of Thrombin by N3-Cyclopropyl-7-{[4-(1-methylethyl)phenyl]methyl}-7H-pyrrolo[3,2-f]quinazoline-1,3-diamine (SCH 79797), a Nonpeptide Thrombin Receptor Antagonist," Biochemical Pharmacology, vol. 60, No. 10, 2000, pp. 1425-1434.
Capodanno et al., "Safety and efficacy of protease-activated receptor-1 antagonists in patients with coronary artery disease: a meta-analysis of randomized clinical trials," Journal of Thrombosis and Haemostasis, vol. 10, 2012, pp. 2006-2015.
De Garavilla et al., "Agonists of proteinase-activated receptor 1 induce plasma extravasation by a neurogenic mechanism," British Journal of Pharmacology, vol. 133, No. 7, 2001, pp. 975-987.
Gras et al., "Atopaxar," Drugs of the Future, vol. 37, No. 2, Feb. 2012, pp. 89-97, XP-002734520.
International Search Report (Form PCT/ISA/210) for International Application No. PCT/EP2014/073453, dated Feb. 10, 2015.
Kosoglou et al., "Pharmacodynamics and pharmacokinetics of the novel PAR-1 antagonist vorapaxar (formerly SCH 530348) in healthy subjects," European Journal of Clinical Pharmacology, vol. 68, No. 3, 2012 (Published online Sep. 21, 2011), pp. 249-258, XP055162389.
Moffatt, "Proteinase-activated receptors in the lower urinary tract," Naunyn-Schmiedeberg's Archive of Pharmacology, vol. 375, No. 1, 2007 (Published online Feb. 10, 2007), pp. 1-9, XP019488494.
Nakahara et al., "Protease-activated receptor-2-mediated contraction of urinary bladder is enhanced in cyclophosphamide-treated rats," Naunyn-Schmiedeberg's Archive of Pharmacology, vol. 369, 2004 (Published online Dec. 12, 2003), pp. 212-219.
Perez et al., "Discovery of Novel Protease Activated Receptors 1 Antagonists with Potent Antithrombotic Activity in Vivo," Journal of Medicinal Chemistry, vol. 52, No. 19, Oct. 8, 2009 (Published on Web Sep. 16, 2009), pp. 5826-5836, XP055116685.
Planty et al., "Exploration of a new series of PAR1 antagonists," Bioorganic and Medicinal Chemistry Letters, vol. 20, No. 5, Mar. 1, 2010 (Available online Jan. 20, 2010), pp. 1735-1739, XP026911345.
Saban et al., "Mandatory role of proteinase-activated receptor I in experimental bladder inflammation," BMC Physiology, vol. 7, No. 4, Mar. 30, 2007, pp. 1-15, XP021023623.
Saban et al., "Transcription factor network downstream of protease activated receptors (PARs) modulating mouse bladder inflammation," BMC Immunology, vol. 8, No. 17, Aug. 17, 2007, pp. 1-21, XP021028148.
Shimizu et al., "Involvement of Bradykinin in Trypsin-Induced Urinary Bladder Contraction in Cyclophosphamide-Treated Rats," Biological and Pharmaceutical Bulletin, vol. 34, No. 7, Jul. 2011 (Published online Apr. 15, 2011), pp. 1122-1125.
Augé et al., "Relevance of the Cyclophosphamide-Induced Cystitis Model for Pharmacological Studies Targeting Inflammation and Pain of the Bladder," European Journal of Pharmacology, vol. 707, 2013 (published online Mar. 26, 2013), pp. 32-40.

(Continued)

*Primary Examiner* — Sudhakar Katakam
(74) *Attorney, Agent, or Firm* — Birch, Stewart, Kolasch & Birch, LLP

(57) ABSTRACT

The present invention relates to the use of PAR1 antagonists, in particular of vorapaxar, of atopaxar and of 3-(2-chlorophenyl)-1-[4-(4-fluorobenzyl)piperazin-1-yl]propenone, or a pharmaceutically acceptable salt thereof, for preventing and/or treating pelvi-perineal functional pathological conditions, and more particularly painful bladder syndrome.

14 Claims, 12 Drawing Sheets

(56) References Cited

OTHER PUBLICATIONS

D'Andrea et al., "Expression of Protease-Activated Receptor-1, -2, -3, and -4 in Control and Experimentally Inflamed Mouse Bladder," American Journal of Pathology, vol. 162, No. 3, Mar. 2003, pp. 907-923.

Dattilio et al., "Up-Regulation of Protease Activated Receptors in Bladder After Cyclophosphamide Induced Cystitis and Colocalization with Capsaicin Receptor (VR1) in Bladder Nerve Fibers," The Journal of Urology, vol. 173, Feb. 2005, pp. 635-639.

Fall et al., "Treatment of Bladder Pain Syndrome/Interstitial Cystitis 2008: Can We Make Evidence-Based Decisions?" European Urology, vol. 54, 2008 (published online Apr. 3, 2008), pp. 65-78.

Monjotin et al., "F16357, A Novel Protease-Activated Receptor 1 Antagonist, Improves Urodynamic Parameters in a Rat Model of Interstitial Cystitis," British Journal of Pharmacology, vol. 173, 2016, pp. 2224-2236.

Mouracade et al., "La Cystite Interstitielle en 2008," Prog. Urol., vol. 18, 2008 (published online May 27, 2008), pp. 418-425 (including an English abstract).

North et al., "P2X Receptors as Drug Targets," Molecular Pharmacology, vol. 83, Apr. 2013, pp. 759-769.

Ortiz, "Chronic Pelvic Pain in Women," American Family Physician, vol. 77, No. 11, Jun. 1, 2008, pp. 1535-1542.

Parsons, "Interstitial Cystitis and Lower Urinary Tract Symptoms in Males and Females—The Combined Role of Potassium and Epithelial Dysfunction," Reviews in Urology, vol. 4, Suppl. 1, 2002, pp. S49-S55.

Peeker et al., "Immunologic and Neurobiologic Characteristics Support that Interstitial Cystitis is a Heterogeneous Syndrome," Urology, vol. 57, Suppl. 6A, Jun. 2001, p. 130.

Rickard et al., "Phospholipid Metabolite Production in Human Urothelial Cells After Protease-Activated Receptor Cleavage," Am. J. Physiol. Renal. Physiol., vol. 52, Nov. 2002 (first published Jul. 9, 2002), pp. F944-F951.

Rickard et al., "Protease-Activated Receptor Stimulation Activates a $Ca^{2+}$-Independent Phospholipase $A_2$ in Bladder Microvascular Endothelial Cells," Am. J. Physiol. Renal. Physiol., vol. 288, Apr. 2005 (first published Nov. 23, 2004), pp. F714-F721.

Saban et al., "Regulatory Network of Inflammation Downstream of Proteinase-Activated Receptors," BMC Physiology, vol. 7, No. 3, Mar. 30, 2007, pp. 1-15.

Vera et al., "Thrombin Induces Macrophage Migration Inhibitory Factor Release and Upregulation in Urothelium: A Possible Contribution to Bladder Inflammation," PLoS One, vol. 5, No. 12, Dec. 31, 2010, pp. 1-8.

Vu et al., "Molecular Cloning of a Functional Thrombin Receptor Reveals a Novel Proteolytic Mechanism of Receptor Activation," Cell, vol. 64, Mar. 22, 1991, pp. 1057-1068.

Wang et al., "Role of Mast Cells and Protease-Activated Receptor-2 in Cyclooxygenase-2 Expression in Urothelial Cells," Am. J. Physiol. Regul. Integr. Comp. Physiol., vol. 297, Oct. 2009 (first published Aug. 12, 2009), pp. R1127-R1135.

\* cited by examiner

USE OF PAR-1 ANTAGONISTS FOR PREVENTING AND/OR TREATING PELVI-PERINEAL FUNCTIONAL PATHOLOGICAL CONDITIONS

The invention concerns PAR-1 antagonists and more particularly vorapaxar, atopaxar and 3-(2-Chloro-phenyl)-1-[4-(4-fluoro-benzyl)-piperazin-1-yl]-propenone or one of the pharmaceutically acceptable salts thereof for use in the prevention and/or treatment of pelvi-perineal functional pathologies.

Pelvi-perineal functional pathologies encompass various pathologies affecting the pelvi-perineal region with the exclusion of cancerous lesions and any proven infectious, metabolic or endocrine pathologies. One pelvi-perineal functional pathology is represented by painful bladder syndrome, also called interstitial cystitis, defined, in the absence of any proven urinary infection or other objective pathologies, as being chronic pelvic pain of more than six months' duration sometimes perceived as bladder-related feelings of pressure or discomfort and accompanied by at least one urinary symptom: persistent strong urge to urinate or pollakiuria. Nocturia very often accompanies this painful bladder syndrome. Pollakiuria is defined as abnormally high urination frequency, more than eight urinations over a 24-hour period. Nocturia is defined as the need to urinate at night waking a patient one or more times. The diagnosis of painful bladder syndrome or interstitial cystitis is based on history-taking and determination of an urination calendar. Clinical examination must have eliminated all other causes of bladder pain, the diagnosis of painful bladder syndrome being a diagnosis of exclusion. In the event of suspected painful bladder syndrome, cystoscopy under general or regional anaesthesia is the key examination for assessment and diagnosis. Conventionally this examination can evidence glomerulations of vesical mucosa with or without Hunner lesions. However cystoscopy may sometimes appear normal at the initial phase with no Hunner lesions. It allows bladder biopsies and bladder hydrodistention to be performed at the same time. Hydrodistention is distention of the bladder with water performed under anaesthesia. Other additional examinations, imaging, urodynamic assessment, biology, cytology are not essential for diagnosis but useful for differential diagnosis since the syndrome of interstitial cystitis remains a diagnosis of exclusion.

There appears to be two categories of patient: those with deteriorations of the bladder wall and in particular with Hunner lesions (20% of cases) and those without. However a continuum exists between these different clinical presentations. It is difficult to know the exact number of persons suffering from this disease which is probably under-diagnosed. Prevalence varies from one country to another. In Europe estimations range from one person affected out of 12,500 to one person out of 1,500. In the United States prevalence is estimated at one person out of about 1,500 persons. While both genders can be affected, 90% of patients suffering from painful bladder syndrome are women. This syndrome can affect persons of any origin, but prevalence of the disease appears higher in western and Scandinavian countries.

The aetiology of painful bladder syndrome remains undetermined. Different studies suggest that its physiopathology is multi-factor. Several pathogenic theories have been put forward even if none of these aetiologies can be held to be the unique aetiological factor. It is most likely that involvements and interactions occur between these different factors.

Infectious mechanism: even if bacterial, viral and fungal analyses in patients suffering from painful bladder syndrome have never been able to incriminate an infectious cause responsible for this disorder. Patients suffering from painful bladder syndrome frequently have a history of bladder infection and for 50% of patients the onset followed after occurrence of an infection. However, up until now no infectious, bacterial or viral factor has been determined as being the cause of the disease and anti-infection treatments are ineffective. Infection with "atypical" germs has been proposed by numerous authors. It has been suggested that the germs found in painful bladder syndrome are not the agents directly responsible but their presence may be responsible for an immunoallergic reaction which plays a role in its onset.

Deterioration of urothelial permeability: the bladder mucosa is coated with a layer of mucin which is composed of numerous glycosaminoglycans and glycoproteins. The characteristic of these glycosaminoglycans is that of having a negative charge enabling them to form an impermeable hydrophobic barrier. This mucin layer therefore prevents urine from entering the urothelium. In patients suffering from painful bladder syndrome this layer is defective and the urothelium is abnormally permeable. As a result, potentially toxic substances in the urine enter into the muscle layer of the bladder wall and depolarise sensitive nerves leading to symptoms of painful bladder syndrome.

Mastocyte reaction; mastocyte cells have been found in the bladder wall in 30 to 65% of patients suffering from painful bladder syndrome. Mastocytes contain cytoplasmic granules comprising substances such as histamine, leukotrienes, prostaglandins and tryptases. All these substances take part in inflammatory reaction. In painful bladder syndrome, oedema, fibrosis and neo-vascularisation may be due to release of these mediators transported by the mastocyte cells. Activation of the mastocytes is dependent on substance P and studies under electron microscopy have shown an increase in nerve endings rich in substance P in contact with the mastocytes. Overall, there seems to exist a major role played by these mastocyte cells in painful bladder syndrome. While the exact primary or secondary role of mastocytes in the aetiology of painful bladder syndrome currently remains a subject of debate, much research is focused on understanding the activation of these cells and their responsibility in symptomatology.

Neuronal mechanism: this is the process whereby the nerves manage to secrete local mediators of inflammation. In painful bladder syndrome there is an increase in sympathetic innervation and activation of puringergic neurotransmission. The existence of local neurogenic inflammation could be the cause of a cascade of chain reactions. This mechanism is described in painful bladder syndrome as well as in other painful syndromes such as fibromyalgia, irritable bowel syndrome. The major component of this mechanism is substance P. This theory is based on the presence of a high concentration of substance P and high number of nerve fibres containing substance P in the bladder wall of patients suffering from painful bladder syndrome. Interestingly it has been shown that the urine concentration of substance P is proportional to pain level.

Auto-immune mechanism: 5% of patients with painful bladder syndrome suffer from an auto-immune disease: lupus, thyroiditis, scleroderma, polyarthritis, Goujerot- Sjogren syndrome. A certain number of studies argue in favour of immune changes in painful bladder syndrome. Nevertheless, an auto-immune mechanism or exact role of the auto-immune mechanism in painful bladder syndrome remains controversial. Deterioration of urothelial permeability may result in inflammatory, auto-immune reactions possibly accounting for the pathogenesis of painful bladder syndrome. The existence of nuclear-factor kappa B activated in bladder biopsies of patients with this syndrome has strengthened this theory. This factor has also been found in other auto-immune diseases including rheumatoid arthritis, inflammatory intestinal diseases and bronchial asthma. However no study has been conclusive and the changes in immune response are not specific and could only be secondary to bladder tissue deterioration.

The symptomatology of painful bladder syndrome is high and above all marked by pain symptoms, the topography of pain is sub-pubic, vesical with irradiation towards the urethra but may also affect the vagina, perineum, rectum, pelvis, sacrum . . . The pain is described as being of a type of burning, gnawing, pressure or discomfort. It is more or less triggered by bladder filling and sometimes relieved on urination. Patients are woken at night by the pain and the urge to urinate. Pain comes in attacks with very painful periods lasting several days and periods when pain is more tolerable but always present.

The constant urinary symptom is the strong, persistent urge to urinate. It can be associated with day-time and night-time pollakiuria. Urgent or pressing needs to urinate may be present but these are encountered above all—this being a diagnosis that must be set aside—in the event of overactive bladder when urgent needs are not painful. Often patients suffering from painful bladder syndrome do not complain of any true urgent need but rather more of a permanent wish to urinate ranging from mere discomfort to true pain which is relieved on urinating. This relief brought by urination accounts for the hurry of these patients to empty their bladder and leads to confusion with urge incontinence. If the need cannot be relieved, the discomfort or pain is generally aggravated without any urine leakage which could on the other hand occur with urge incontinence. This is true for the majority of patients suffering from painful bladder syndrome but it is possible to have painful bladder syndrome and associated urge incontinence, which complicates diagnostic assessment.

The clinical syndrome of overactive bladder may have several causes: a neurological cause (medullar trauma, Parkinson's disease, multiple sclerosis . . . ), a psycho-behavioural cause or it may be idiopathic coming within the nosology realm of pelvi-perineal functional pathologies. The clinical syndrome of overactive bladder may or may not be accompanied by non-inhibited contractions of the detrusor which is the bladder muscle. However, not every contraction of the detrusor is accompanied by involuntary urine leakage. Several contractions, probably most contractions, occur against a closed urinary tract sphincter. From a physiopathological viewpoint, this situation may be equivalent to urinary infra-vesical obstruction. Over time progressive hypertrophy of the smooth muscle bundles may occur. At cystoscopy, depending on frequency, amplitude and duration of these contractions, the bladder wall will exhibit trabeculations of greater or lesser extent possibly even causing a multi-diverticular bladder. In time, fibre degeneration may be produced within these hypertrophied muscle bundles replacing the smooth muscle fibres by deposits of collagen and fibrous tissue. The bladder will become increasingly less distensible, its capacity increasingly smaller and its contractility increasingly less effective. This process can therefore lead to a bladder of small capacity that is non-compliant and acontractile (or at least having deficient contractility). The syndrome of overactive bladder having variable expression groups together the urge incontinencies associated or not with incontinence and/or day-time or night-time pollakiuria. There is not only one symptom that is pathognomonic of overactive bladder, but rather a set of symptoms which may indicate this pathology: the presence of a triad of symptoms may reasonably suggest overactivity.

Urge incontinencies or pressing needs correspond to an urgent need to urinate accompanied by fear of leakage. They may or may not be followed by pressing urination which cannot be controlled or delayed by the patient, thereby causing leakage through pressing need.

Amongst pelvi-perineal functional pathologies mention can also be made of incontinence.

Urinary incontinence is defined as accidental or involuntary loss of urine via the urethra. This disorder affects both men and women and the cause is often multifactorial. The prevalence of this disorder represents about 3 million persons in France. It is particularly frequent in the elderly. Urinary continence requires a properly functioning pelvic floor, sphincter integrity and nerve controlling of these and of the detrusor. Any deterioration of one of these structures can lead to incontinence. A distinction is conventionally made between several forms of incontinence:

stress urinary incontinence, characterized by urine leakage on physical activity, coughing and sneezing without any prior urging;

urge urinary incontinence characterized by urine leakage accompanied by or immediately preceded by an urgent pressing need to urinate, leading to urination that cannot be delayed or retained;

mixed urinary incontinence combines the two predefined types of incontinence;

enuresis is particularly seen in children with involuntary urination at night.

Aside from the discomfort felt, urinary incontinence can have psychological (anxiety, depression) and social (withdrawal) repercussions. Promoting factors of urinary incontinence include age, stress, obesity, neurological disorders, infection, prolapse or slackening of the sphincter or pelvic floor muscles after abdominal surgery or childbirth for example.

Anal incontinence corresponds to the involuntary emission of gases and/or liquid and/or solid faeces, whereas faecal incontinence excludes the emission of gases. Anal incontinence does not only concern the elderly but also persons of any age, women being more often affected than men. Childbirth and the onset of menopause are factors promoting this incontinence. The other risk factors include some traumas or surgical procedures at the anal sphincter. However incontinence can also result from some neurological pathologies (stroke, diabetes, multiple sclerosis . . . ), from certain surgical anal procedures or congenital malformation. Faecal incontinence may also be accompanied by prolapse of the rectum or it may be the symptom of another disease such as cancer for example.

Chronic pelvi-perineal pain including painful bladder syndrome is pain characterized by chronicity (more than six months), absence of malignant pathology and its topography: the pelvis and the perineum. There is major discrepancy between the extent of patient complaint and the absence of lesion factors likely to justify the complaint. One half of patients complain of isolated pelvic pain, one quarter of patients also suffer from irritable bowel syndrome, 10% of patients suffer from clinical overactive bladder syndrome and the remaining 15% accumulate the 3 syndromes. Associations are very frequent between all painful pathologies: painful bladder syndrome, vestibulodynia, irritable bowel syndrome, pelvic pain, fibromyalgia and myofascial pain. Patients complain of allodynia i.e. pain elicited by a stimulus which is not normally felt to be painful. There exists a predisposition promoting the expression of pain in the event of fibromyalgia, chronic fatigue syndrome, migraine, complex regional pain syndrome, anxiety, depression. Painful bladder syndrome takes on all its meaning here since it can cover true diseases of the vesical wall with intolerance to filling of the bladder but it can also cover bladder hypersensitivities of which the root cause is not necessarily within the bladder.

As for many diseases for which the exact causes are unknown, there is no treatment allowing the curing of painful bladder syndrome. However several therapeutic options provide relief to patients by reducing the symptoms. Initially, behavioural changes and self-care can improve the symptoms and must be applied as much as possible. Also, stress management must be encouraged to manage exacerbation of symptoms induced by stress. Physical therapies using suitable manual techniques can also be proposed.

At pharmacological level it is possible to use drugs essentially acting on pain and inflammation, and directly on the deteriorated wall of the bladder for protection or reconstitution thereof. Non-steroidal anti-inflammatories can relieve pain and inflammation but they are rarely sufficient and they do not have a lasting effect. They are generally well tolerated but may lead to adverse side effects. In general, all pain-relieving medication can be tried. Paracetamol and opiate analgesics, morphine derivatives may be efficient alone or in association with other pain relievers. Tricyclic antidepressants administered at lower doses than those used to treat depression also act on pain. The administration of antihistaminics may be effective, the local secretion of histamine by the mastocytes possibly having a local role in inflammation. It is also possible to administer pentosanpolysulfate; this is a polysaccharide having a structure similar to that of glycosaminoglycans and is eliminated in the urines and is thought to reconstitute the deteriorated layer.

Hydrodistention may give patients relief for a few weeks but the effects fade with repeat procedures and repetition thereof promotes the risk of onset of a compliance disorder. Instillations of different products can be proposed; local treatment having the advantage of allowing direct application of the product in contact with the mucosa and of reducing systemic exposure. Instillation is a therapeutic method whereby a solution is inserted into a natural conduit or cavity of the body to wash, disinfect and treat this conduit or this cavity. Administration of the solution into the bladder uses a catheter. Among those products having exhibited efficiency is heparin which has anti-inflammatory and protective properties and contributes towards temporarily reinforcing the deteriorated glycoprotein layer. For lack of any sufficiently robust studies, it is difficult correctly to evaluate the benefits and risks of this treatment. It would seem that it is able only to improve a subset of patients. It is also possible to instil local anaesthetic products into the bladder such as lidocaine to reduce pain. Dimethyl sulfoxide has shown an effect against pain, in particular in association with corticosteroids, heparin and/or a local anaesthetic. Results are generally good at the start of treatment but instillations need to be repeated, as for most other medications. However this product is highly ill-tolerated in some patients in whom it causes burns and can even aggravate the symptoms on initiation of the treatment. Hyaluronic acid or chondroitin sulfate said to have a restorative effect on the deteriorated bladder wall have proved their efficacy in some patients.

Instillation of products into the bladder may provide relief and can therefore be proposed despite the disadvantage of requiring urinary catheterization with its risks of trauma and sepsis.

Surgery is only to be envisaged as a last resort when all other treatments have failed and symptoms have become extremely incapacitating. Surgery is fairly heavy, traumatic and at times only provides little or no improvement. The different possible procedures range from partial cystectomy to the most radical total cystectomy with urethrectomy.

Numerous treatments are therefore proposed to manage painful bladder syndrome but the efficacy of these different treatments is modest with trials in a small number of patients, these not always being part of prospective randomised trials. It is therefore clearly apparent that the treatments offered to persons suffering from this syndrome are far from being sufficient. There is therefore a major medical need and hence a need for novel medicinal products having the least possible adverse effects since they are intended for physiologically weakened persons.

PAR receptors (protease-activated receptors) are heptahelical receptors coupled to trimeric G proteins: a distinction is made between PAR1 receptors composed of 425 amino acids, PAR2 with 397 amino acids, PAR3 composed of 374 amino acids and PAR4 with 385 amino acids. Thrombin activates PAR1, PAR3 and PAR4 by cleaving their extracellular N-terminal end between arginine 41 and serine 42. The cleaved peptide has no particular activity, the new N-terminal end of the receptor acts as agonist by folding towards the cell surface and interacting with the extracellular domains.

PAR1 plays a key role in platelet activation at low thrombin concentrations whereas PAR4 reacts to strong concentrations. The role of PAR1 has been determined in the field of vascular biology and atherothrombosis. PAR1 antagonists have emerged as novel, promising antithrombotics acting via oral route. Mention can be made of vorapaxar, atopaxar which have provided promising clinical data (Capodanno et al. 2012). Vorapaxar was given FDA authorisation in 2014 for the indication "reduction of thrombotic events in patients with a history of myocardial infarction or peripheral arterial disease". Atopaxar is currently no longer under development as inhibitor of platelet aggregation.

On the bladder wall PAR1 and PAR2 are expressed both on urothelial cells and also on the detrusor cells (Saban et al. 2007).

Studies have shown the major involvement of PAR2 in bladder contractility (Nakahara et al. 2004).

It has been demonstrated that PAR activation by thrombin induces inflammation of the bladder in different animal models (De Garavilla et al. 2007; Saban et al. 2007).

The inventors have shown that a selective antagonist of PAR1 receptors forms an innovative therapeutic approach to treatment of inflammation and associated pain in pelviperineal functional pathologies and in particular in painful bladder syndrome.

Unexpectedly the inventors have discovered that vorapaxar, atopaxar and 3-(2-Chloro-phenyl)-1-[4-(4-fluorobenzyl)-piperazin-1-yl]-propenone, or one of the pharmaceutically acceptable salts thereof, is capable of protecting the bladder whilst efficiently reducing its myogenic contractile responses.

Vorapaxar is described in patent application WO 03089428: it is ethyl N-[(3R,3aS,4S,4aR,7R,8aR,9aR)-4-[(E)-2-[5-(3-fluorophenyl)-2-pyridyl]vinyl1-3-methyl-1-oxo-3a,4,4a,5,6,7,8,8a,9,9a-decahydro-3H-benzo[f]isobenzofuran-7-yl]carbamate.

Atopaxar is [(1-(3-tert-butyl-4-methoxy-5-morpholinophenyl)-2-(5,6-diethoxy-fluoro-1-imino-1,3-dihydro-2H-isoindol-2yl) ethanone hydrobromide.

3-(2-Chloro-phenyl)-1-[4-(4-fluoro-benzyl)-piperazin-1-yl]-propenone represented by formula:

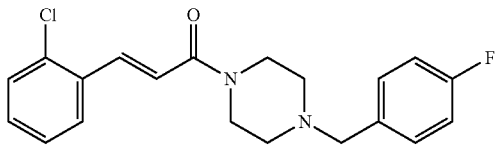 [SMILES: O=C(/C=C/c1ccccc1Cl)N1CCN(Cc2ccc(F)cc2)CC1]

the pharmaceutically acceptable salts thereof and its use as platelet aggregation inhibitor in the treatment both curative and preventive of arterial or venous thrombosis, stable angina, heart beat disorders, myocardial infarction, hypertension, heart failure, stroke, acute coronary syndromes, to inhibit the proliferation of smooth muscle cells (restenosis), in the curative and preventive treatment of inflammatory disorders, lung diseases, gastro-intestinal diseases, development of fibrosis in patients suffering from chronic liver disease, skin diseases, for the curative and preventive treatment of the proliferation of endothelial, fibroblast, cardiac fibroblast, glial, smooth muscle or cancer cells—are described in patent WO 2007/147824.

In the present invention the term "pharmaceutically acceptable" refers to molecular entities and compositions which do not produce any adverse, allergic effect or other adverse reaction when administered to a human being. When used herein the term "pharmaceutically acceptable excipient" includes any diluent, adjuvant or excipient such as preserving agents, fillers, disintegrating, wetting, emulsifying, dispersing, antibacterial or antifungal agents, or agents allowing delayed absorption and intestinal and digestive resorption. The use of these media or vectors is well known to persons skilled in the art.

The pharmaceutically acceptable salts for therapeutic use of a compound of the present invention include conventional non-toxic salts of the compound of the invention such as those formed from organic or inorganic acids. As examples, mention can be made of salts derived from inorganic acids such as hydrochloric, hydrobromic, phosphoric, sulfuric acids and those derived from organic acids such as acetic, trifluoroacetic, propionic, succinic, fumaric, malic, tartaric, citric, ascorbic, maleic, glutamic, benzoic, salicylic, toluenesulfonic, methanesulfonic, stearic, lactic acids.

These salts can be synthesised from a compound of the invention containing a base part and the corresponding acids following conventional chemical methods.

The solvates acceptable for therapeutic use of a compound of the present invention comprise conventional solvates such as those formed at the last step in the preparation of a compound of the invention due to the presence of solvents. As examples, mention can be made of solvates due to the presence of water or ethanol.

Vorapaxar, atopaxar and 3-(2-Chloro-phenyl)-1-[4-(4-fluoro-benzyl)-piperazin-1-yl]-propenone are selective PAR1 antagonists.

The PAR1 antagonists known to date are N3-cyclopropyl-7-([4-(1-methylethyl)phenyl]methyl)-7H-pyrrolo[3,2-f]guinazoline-1,3-diamine (SCH-79797), vorapaxar (SCH-530348), atopaxar (E5555) and SCH-602539.

A subject of the invention is the use of a PAR1 antagonist as medication in the prevention and/or treatment of pelviperineal functional pathologies.

A subject of the invention is the use of vorapaxar as medication in the prevention and/or treatment of pelviperineal functional pathologies.

A subject of the invention is the use of atopaxar as medication in the prevention and/or treatment of pelviperineal functional pathologies.

A subject of the invention is the use of 3-(2-Chloro-phenyl)-1-[4-(4-fluoro-benzyl)-piperazin-1-yl]-propenone as medication in the prevention and/or treatment of pelviperineal functional pathologies.

A subject of the invention is the use of a PAR1 antagonist as medication in the prevention and/or treatment of painful bladder syndrome.

A subject of the invention is the use of vorapaxar as medication in the prevention and/or treatment of painful bladder syndrome.

A subject of the invention is the use of atopaxar as medication in the prevention and/or treatment of painful bladder syndrome.

A subject of the invention is the use of 3-(2-Chloro-phenyl)-1-[4-(4-fluoro-benzyl)-piperazin-1-yl]-propenone as medication in the prevention and/or treatment of painful bladder syndrome.

A subject of the invention is the use of a PAR1 antagonist as medication in the prevention and/or treatment of overactive bladder syndrome.

A subject of the invention is the use of vorapaxar as medication in the prevention and/or treatment of overactive bladder syndrome.

A subject of the invention is the use of atopaxar as medication in the prevention and/or treatment of overactive bladder syndrome.

A subject of the invention is the use of 3-(2-Chloro-phenyl)-1-[4-(4-fluoro-benzyl)-piperazin-1-yl]-propenone as medication in the prevention and/or treatment of overactive bladder syndrome.

A further subject of the invention concerns the use of a PAR1 antagonist in patients presenting with urinary incontinence and/or anal or faecal incontinence.

A further subject of the invention concerns the use of vorapaxar in patients presenting with urinary incontinence and/or anal or faecal incontinence.

A further subject of the invention concerns the use of atopaxar in patients presenting with urinary incontinence and/or anal or faecal incontinence.

A further subject of the invention concerns the use of 3-(2-Chloro-phenyl)-1-[4-(4-fluoro-benzyl)-piperazin-1-yl]-propenone in patients presenting with urinary incontinence and/or anal or faecal incontinence.

A further subject of the invention concerns the use of a PAR1 antagonist in patients presenting with chronic pelvi-perineal pain.

A further subject of the invention concerns the use of vorapaxar in patients presenting with chronic pelvi-perineal pain.

A further subject of the invention concerns the use of atopaxar in patients presenting with chronic pelvi-perineal pain.

A further subject of the invention concerns the use of 3-(2-Chloro-phenyl)-1-[4-(4-fluoro-benzyl)-piperazin-1-yl]-propenone in patients presenting with chronic pelvi-perineal pain.

The present invention further concerns a pharmaceutical composition comprising a PAR1 antagonist as active ingredient and at least one pharmaceutically acceptable excipient for use thereof as medication in the prevention and/or treatment of pelvi-perineal functional pathologies, in particular OF painful bladder syndrome, overactive bladder syndrome, chronic pelvi-periTOneal pain. The present invention also concerns a pharmaceutical composition comprising a PAR1 antagonist as active ingredient and at least one pharmaceutically acceptable excipient for use thereof as medication in patients presenting with urinary incontinence and/or anal or faecal incontinence.

The pharmaceutical compositions of the present invention can be formulated for administration to human beings. The compositions of the present invention can be administered via oral, sublingual, sub-cutaneous, intramuscular, intravenous, transdermal, local or rectal route. In this case the active ingredient can be administered to human beings in unit administration forms in a mixture with conventional pharmaceutical substrates. Suitable unit administration forms include forms via oral route such as tablets, capsules, powders, granules and solutions or oral suspensions, sublingual and buccal administration forms, subcutaneous or transdermal, topical, intramuscular, intravenous, intra-nasal or intra-ocular administration forms, intra-vesical, intramural or rectal administration forms.

When a solid composition is prepared in tablet form, the main active ingredient is mixed with a pharmaceutical carrier such as gelatine, starch, lactose, magnesium stearate, talc, gum arabic, silica or the like. The tablets can be coated with sucrose or other suitable materials or they can be treated so that they have extended or delayed release and continuously release a predetermined amount of active ingredient. A capsule preparation is prepared by mixing the active ingredient with a diluent and pouring the mixture obtained into hard or soft capsules.

A preparation in syrup or elixir form can contain the active ingredient together with a sweetener, antiseptic, taste enhancer and suitable colouring agent.

Water-dispersible powders or granules can contain the active ingredient in a mixture with dispersion or wetting agents, or suspending agents, and also with taste enhancers or sweeteners.

For rectal administration gels, creams, powders, suspensions, solutions, foams or suppositories are used which are prepared with binders which melt at rectal temperature e.g. cocoa butter or polyethylene glycols.

For parenteral administration (intravenous, intramuscular, intradermal, sub-cutaneous), intra-nasal, intraocular, intravesical or intramural administration the use is made of aqueous suspensions, isotonic saline solutions or sterile, injectable solutions containing pharmacologically compatible dispersion agents and/or wetting agents.

The active ingredient can also be formulated in the form of microcapsules, optionally with one or more added substrates.

Suitable formulations for the selected administration form are known to persons skilled in the art and described for example in: Remington, The Science and Practice of Pharmacy, 19$^{th}$ Edition, 1995, Mack Publishing Company.

Advantageously, the pharmaceutical composition of the present invention is intended for administration via local route: the term endovesical is used, the pharmaceutical composition of the present invention is intended to be used in endovesical administration form. Among endovesical treatments preference is given to vesical instillation and/or intramural injection i.e. administration into the thickness of the bladder wall.

The dosages of the PAR1 antagonist in the compositions of the invention can be adjusted to obtain an amount of substance that is effective to obtain the desired therapeutic response for a composition particular to the method of administration. The effective dose of the compound of the invention varies as a function of numerous parameters such as the chosen administration route, patient weight, age, gender, type of pathology, type of applied treatment(s) and sensitivity of the person to be treated. As a result, the optimal dosage must be determined by the specialist in relation to parameters considered to be relevant. Although effective doses may vary in large proportions, the daily doses could range from 0.1 mg to 1000 mg every 24 hours, and preferably between 1 and 200 mg for an adult of 70 kg average weight, taken at one or more times.

The following examples allow better comprehension of the invention without limiting the scope thereof.

EXAMPLE 1

Effect of 3-(2-Chloro-phenyl)-1-[4-(4-fluoro-benzyl)-piperazin-1-yl]-propenone on a Rat-isolated Bladder Model (Shimizu et al., Biol. Pharm. Bull. 34(7):1122-1125, 2011)

Purpose of the experiment: Evaluate the role of 3-(2-Chloro-phenyl)-1-[4-(4-fluoro-benzyl)-piperazin-1-yl]-propenone on the amplitude of bladder contraction induced by trypsin and TFLLR. The experiment was led in parallel on naive bladders and on bladders subjected to inflammation procedure. The effect of the compound of the invention was compared with that of a reference PAR1 antagonist: compound SCH203099, (Ahn et al. Biochem. Pharmacol. 60(10: 1425-1434, 2000).

Protocol

To induce inflammation of the bladder, cyclophosphamide was bilaterally injected into the rats (Female Wistar Han rats weighing 250 to 275g on the day of the experiment, obtained from Charles River laboratory, France) via intraperitoneal route at a dose of 150 mg/kg in a final volume of 5 mL/kg.

Pain evaluation was conducted 2 hours after cyclophosphamide administration.

In naive rats (no administration of cyclophosphamide) or 24 hours after administration of cyclophosphamide, the animals were anaesthetised with pentobarbital (60 mg/kg) and euthanized. The bladder was rapidly taken and placed in modified Krebs-Henseleit oxygenated solution having the following composition (mM): NaCl 114; KCl 4.7; $CaCl_2$ 2.5; $MgSO_4$ 1.2; $KH_2PO_4$ 1.2; $NaHCO_3$ 25 and glucose 11.7 (pH 7.4 with 95% $O_2$ and 5% $CO_2$). The bladder was cleaned of conjunctive tissue, weighed, the distal and proximal portions removed and the bladder cut in longitudinal direction into two equal strips. These strips were attached with silk thread and immersed in a 10 mL isolated organ bath (EMKA Technologies) containing the Krebs-Henseleit oxygenated solution with 95%:5% mixture of $O_2/CO_2$ held at 37° C. The bladder strips were connected via the silk thread to isometric sensors (IT50 model, EMKA Technologies)

connected to amplifiers (EMKA Technologies). Contractile responses were recorded using IOX2® software (EMKA Technologies).

For an initial stabilisation period of at least 90 minutes, rinsing operations were carried out every 15 minutes and the tensioning of each bladder strip readjusted to 1.0 g. The strips were then exposed to 50 mM KCl to verify their viability. If the contraction amplitude of the strips was less than 1.0 g, the tissues were discarded and not included in the experiment. After a second stabilisation and washing period of at least 45 minutes, a concentration of the compound of the invention or of the reference product (SCH203099) or of the vehicle was incubated for 30 minutes. A concentration-accumulative response curve to the selective agonist PAR1, to TFLLR (0.1 µM to 0.1 mM) or to trypsin (10 U to 10,000 BAEE U/mL) was plotted.

Results

In the presence of 3000 BAEE U/mL trypsin, inflammation increased bladder contractility due to PAR activation by a factor of 2.5. Contraction amplitude was 0.99±0.20 g for the naive vehicle group versus 2.73±0.34 g for the vehicle group treated with cyclophosphamide.

Figure 1:
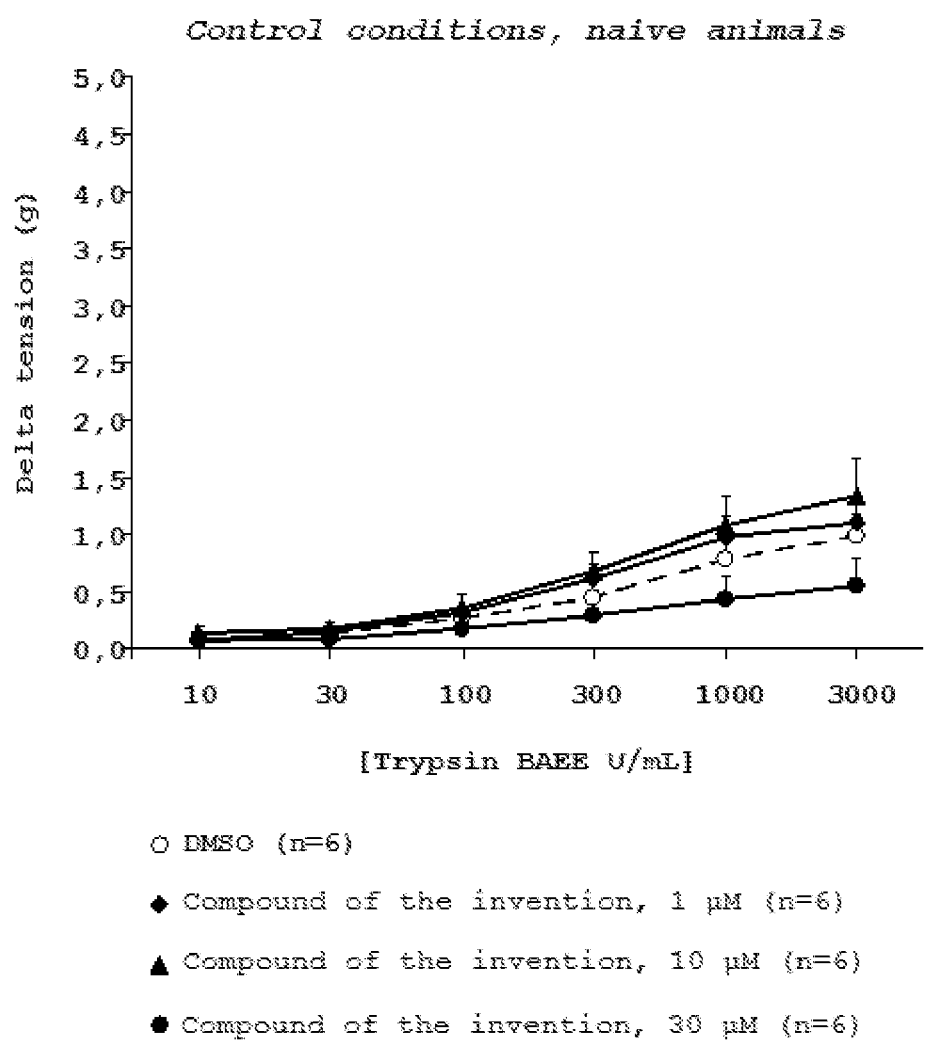
FIG. 1 shows a compound of the invention antagonizes trypsin-induced bladder contractions only at strong concentrations in naïve animals as shown in FIG. 1.

The compound of the invention antagonises trypsin-induced bladder contraction only at strong concentrations in naïve animals as shown in FIG. 1. The amplitude of bladder contraction was divided by two with the compound of the invention at 30 µM versus vehicle (0.55±0.24 g versus 0.99±0.20 g) and nothing was observed at the other concentrations of the compound of the invention.

Figure 2:
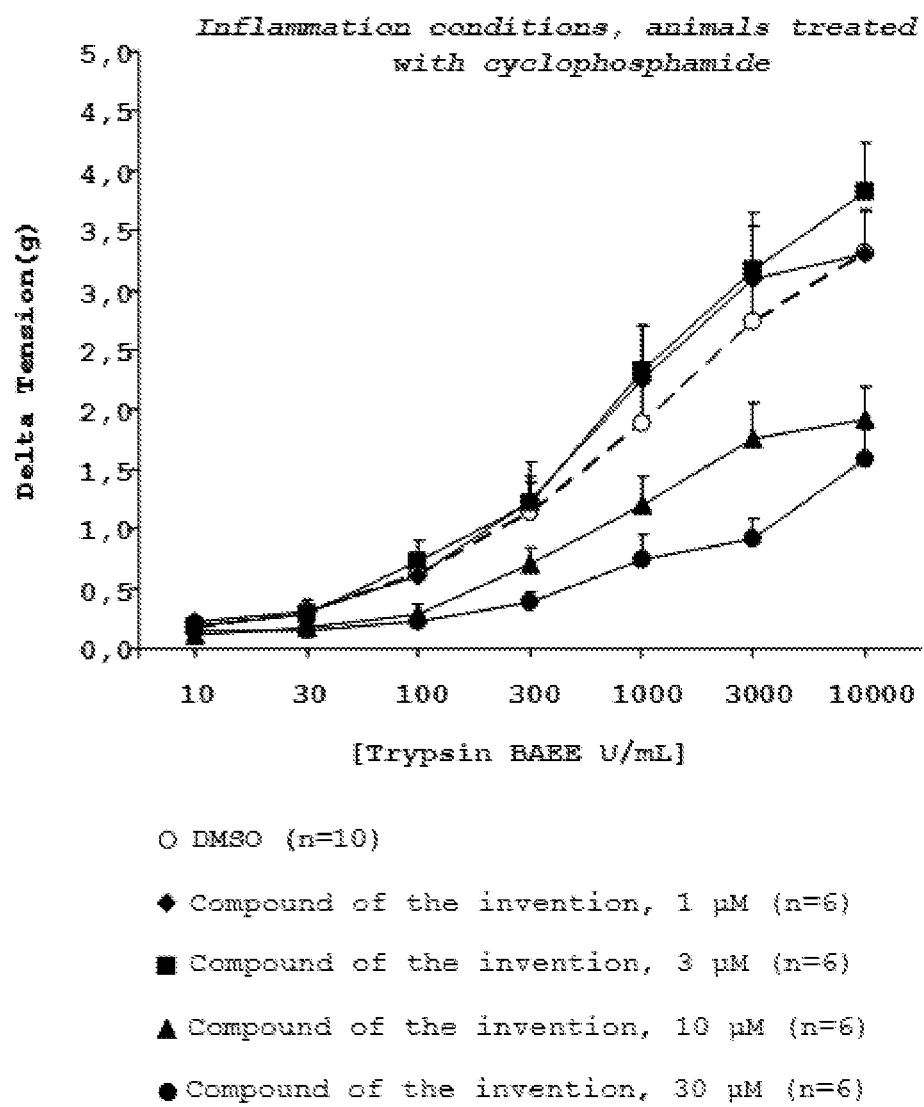
FIG. 2 shows a compound of the invention has concentration-dependent antagonist action on trypsin-induced bladder contraction under inflammation conditions.

The compound of the invention has concentration-dependent antagonist action on trypsin-induced bladder contraction under inflammation conditions (FIG. 2). Up to 3 µM the compound of the invention appears to be inactive, at 10 µM the compound of the invention reduces bladder contraction by 35% (1.76±0.30 g versus 2.73±0.34 g). At 30 µM the compound of the invention reduces bladder contraction by about 70% (0.92±0.17 g versus 2.73±0.34g).

Figure 3:
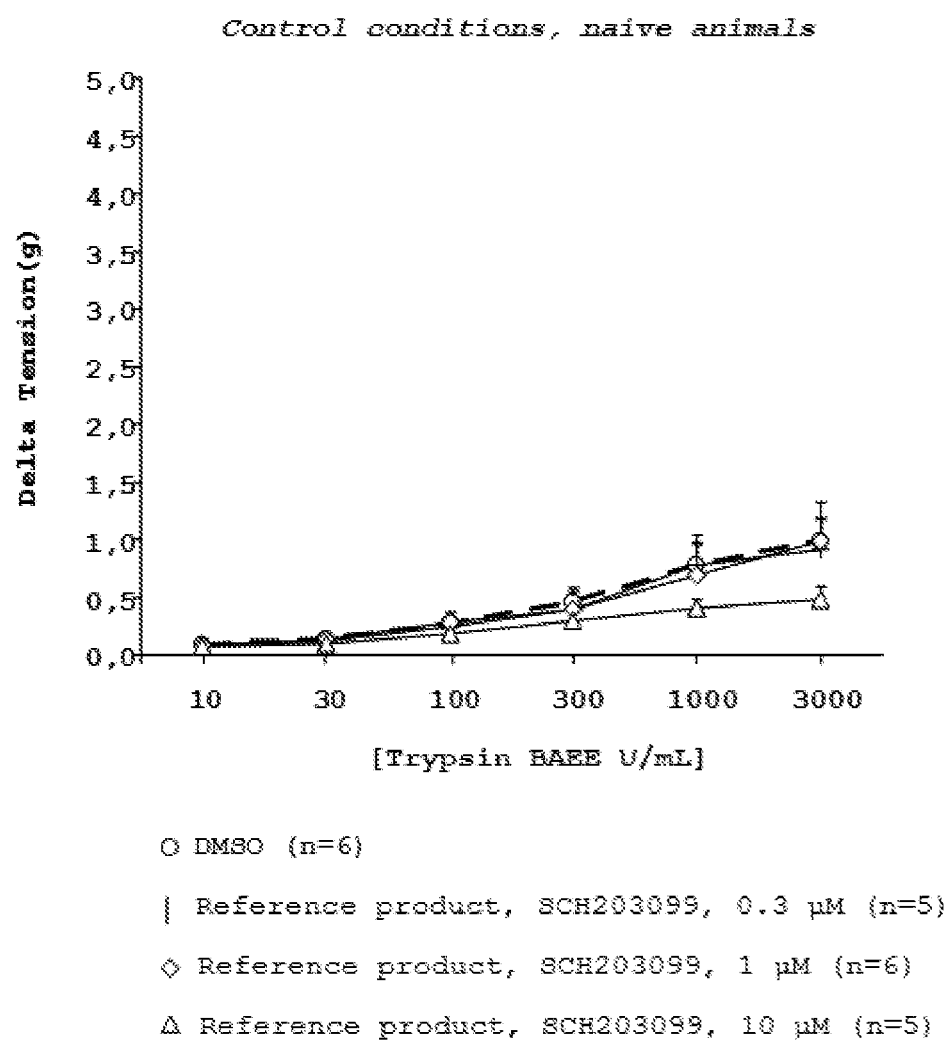
FIG. 3 shows reference product (SCH203099) antagonized trypsin-induced bladder contraction only at strong concentrations in naïve animals.

The reference product (SCH203099) antagonised trypsin-induced bladder contraction only at strong concentrations in naive animals (FIG. 3). The amplitude of bladder contraction was divided by two in the presence of 10 µM SCH203099 versus the vehicle (0.48±0.11 g versus 0.99±0.20 g) and nothing was observed at the other concentrations of SCH203099.

Figure 4:
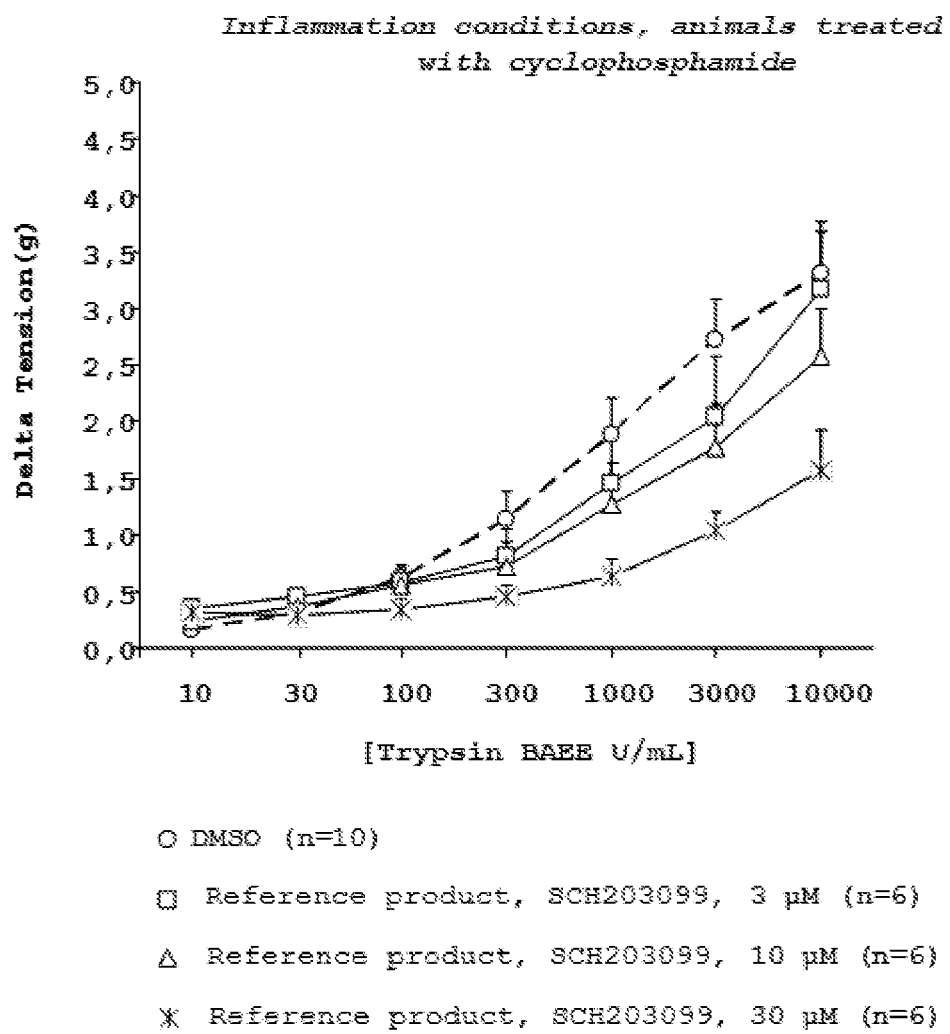
FIG. 4 shows reference product (SCH203099) has concentration-dependent antagonist action on trypsin-induced bladder contraction under inflammation conditions.

Compound SCH203099 had concentration-dependent antagonist action on trypsin-induced bladder contraction under inflammation conditions (FIG. 4). A 25% reduction was observed with 3 µM SCH203099 (2.05±0.53 g versus 2.73±0.34 g), a 35% reduction was observed in the presence of 10 µM SCH203099 (1.77±0.38 g versus 2.73±0.34 g) and 30 µM SCH203099 reduced bladder contraction by 60% (1.04±0.16 g versus 2.73±0.34 g).

In the presence of 100 µM TFLLR, inflammation increased bladder contractility due to PAR1 activation by a factor of 2. The amplitude of contraction was 0.59±0.14 g for the naive vehicle group versus 1.10±0.18 g for the vehicle group treated with cyclophosphamide.

Figure 5:
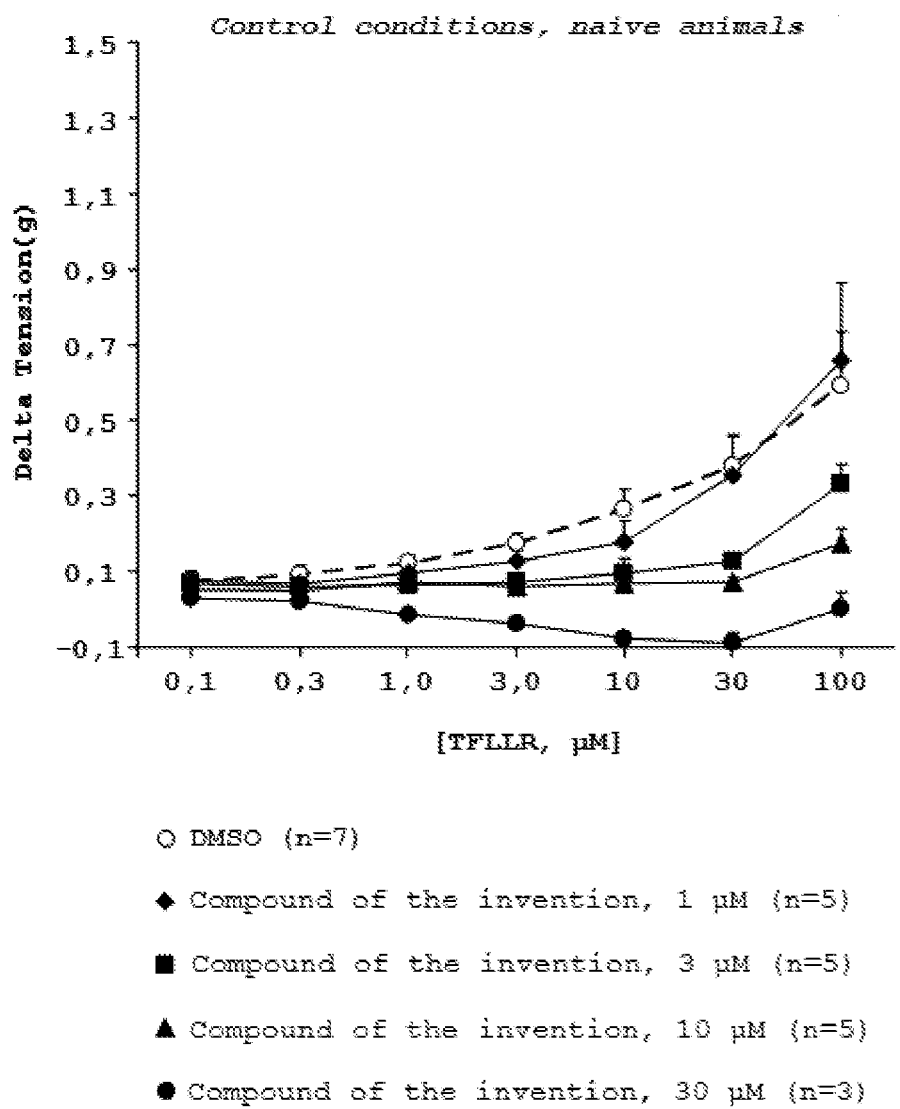
FIG. 5 shows a compound of the invention has concentration-dependent antagonist action on TFLLR-induced bladder contraction in naïve animals.

The compound of the invention has concentration-dependent antagonist action on TFLLR-induced bladder contraction in naive animals. At 1 µM the compound of the invention appeared to be inactive, at 3 µM a 45% reduction in bladder contraction was observed (0.33±0.05 g versus 0.59±0.14 g). At 10µM the compound of the invention reduced bladder contraction by 70% (0.18±0.04 g versus 0.59±0.14 g). At 30 µM the compound of the invention completely abolished bladder contraction (0.00±0.04 g versus 0.59±0.14 g) even with tissue relaxation during the experiment (FIG. 5).

Figure 6:
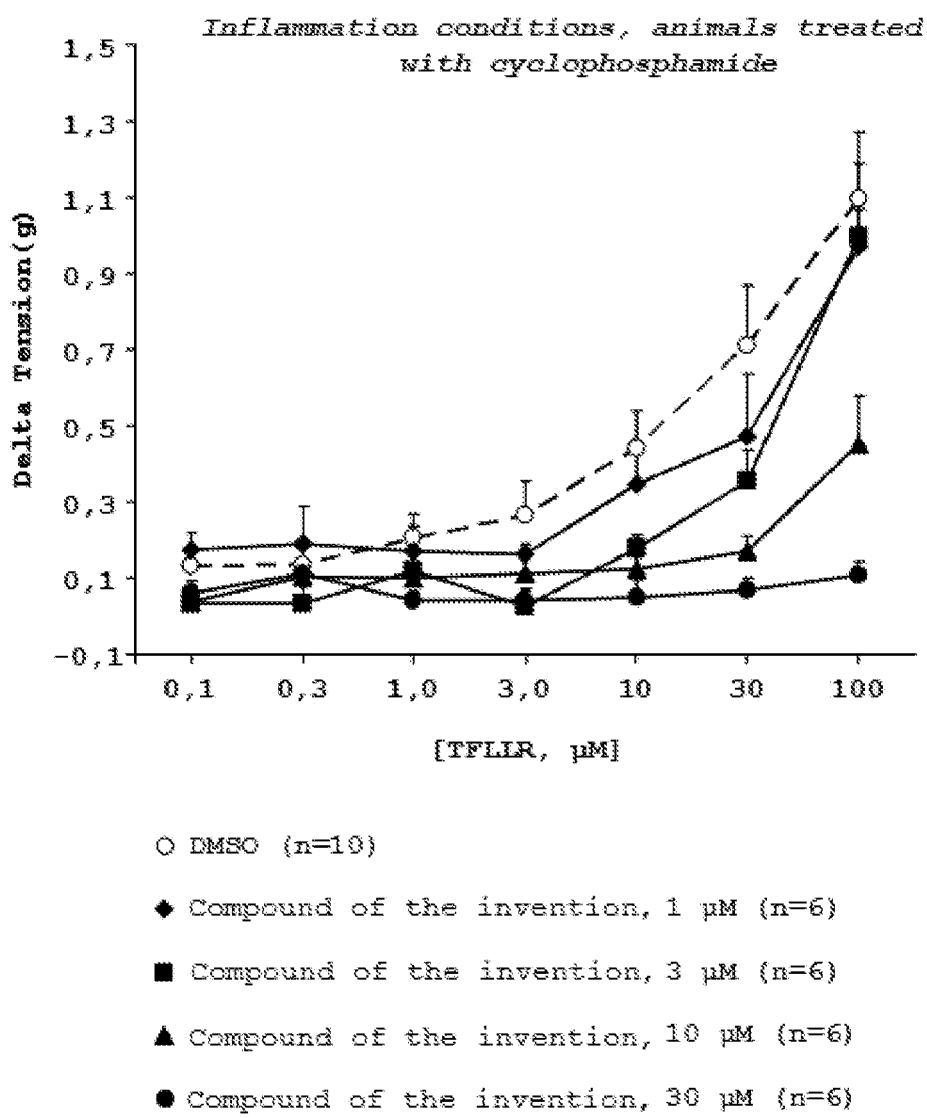
FIG. 6 shows a compound of the invention has concentration-dependent antagonist action on TFLLR-induced bladder contraction under inflammation conditions.

The compound of the invention also has concentration-dependent antagonist action on TFLLR-induced bladder contraction under inflammation conditions (FIG. 6). Up to 3 µM no conclusive effect (only 10% reduction), at 10 µM the compound of the invention reduced bladder contraction by 60% (0.45±0.13 g versus 1.10±0.18 g) and at 30 µM the compound of the invention reduced contractile response by 90% (0.11±0.04 g versus 1.10±0.18 g).

Figure 7:
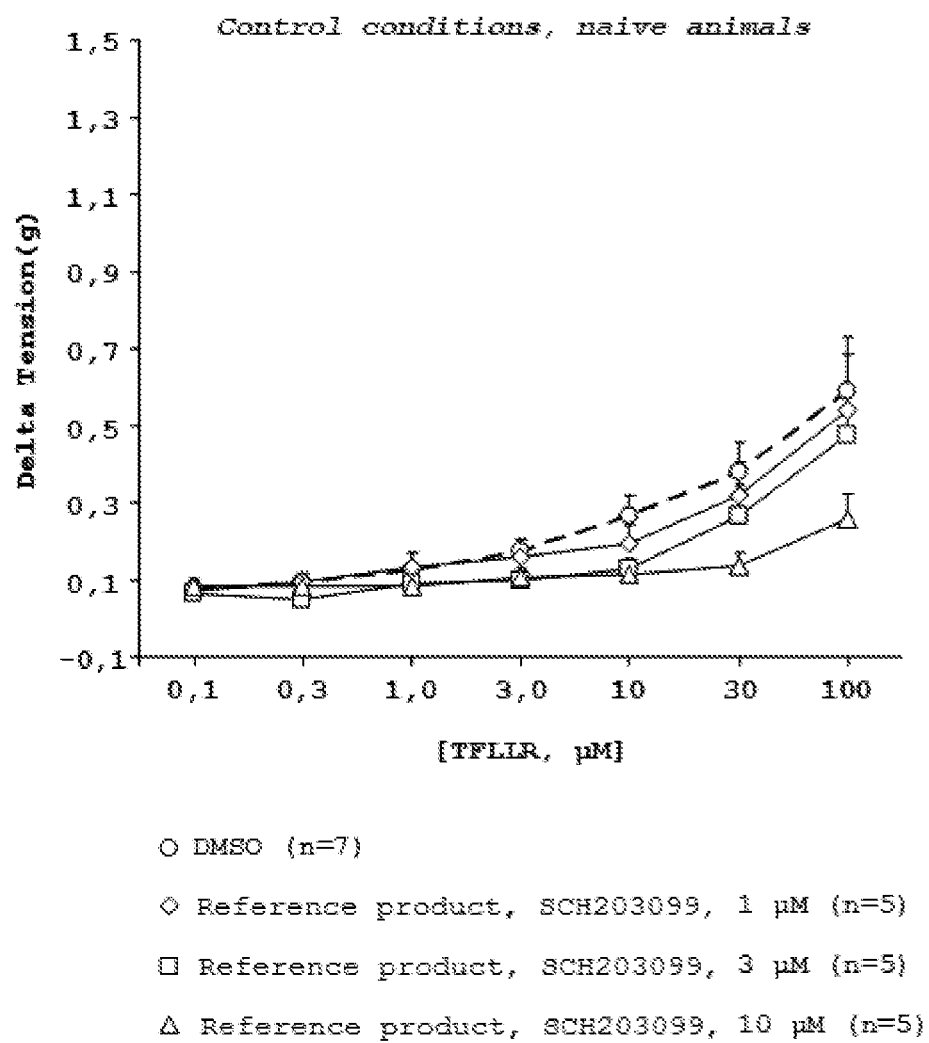
FIG. 7 shows reference product (SCH203099) antagonized TFLLR-induced bladder contraction only at high concentrations in naïve animals.

The reference product (SCH203099) antagonised TFLLR-induced bladder contraction only at high concentrations in naive animals (FIG. 7). The amplitude of bladder contraction was divided by two in the presence of 10 µM SCH203099 versus the vehicle (0.26±0.07 g versus 0.59±0.14 g) and nothing was observed at the other concentrations of SCH203099.

Figure 8:
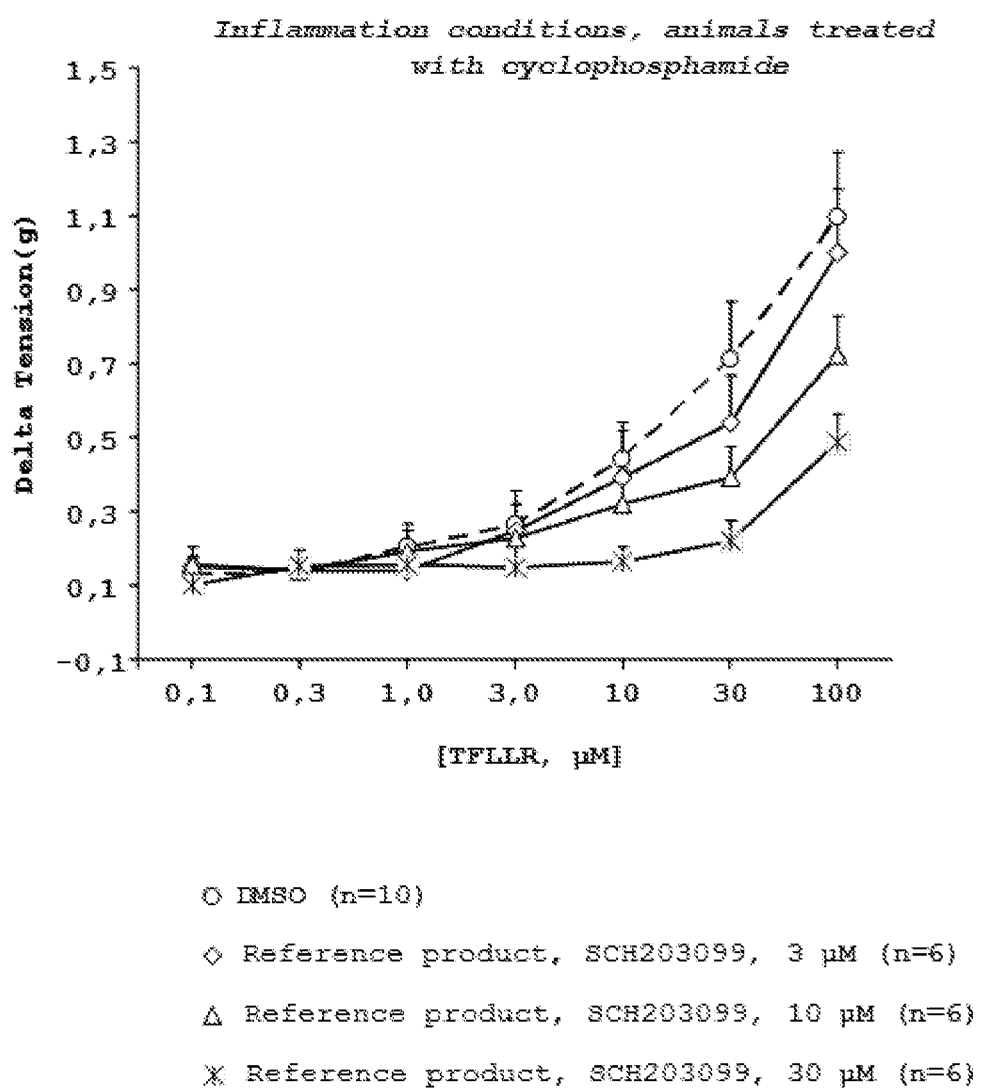
FIG. 8 shows reference product (SCH203099) has concentration-dependent antagonist action on TFLLR-induced bladder contraction under inflammation conditions.

Compound SCH203099 has concentration-dependent antagonist action on TFLLR-induced bladder contraction under inflammation conditions (FIG. 8). At 3 µM SCH203099 no conclusive effect was observed (10% reduction). A 35% reduction was noted in the presence of 10 µM SCH203099 (0.73±0.10 g versus 1.10±0.18 g) and 30 µM SCH203099 reduced bladder contraction by 55% (0.49±0.08 g versus 1.10±0.18 g).

To summarise, trypsin-induced bladder contractions are antagonised in similar fashion by the reference product (SCH203099) and the compound of the invention. On the other hand with bladder contractions induced by the PAR1 agonist, the compound of the invention has a more powerful effect on inflamed bladders.

The inventors have therefore surprisingly shown that the compound of the invention efficiently reduces exacerbated contractile responses of an inflamed and/or overactive bladder i.e. the compound of the invention appears to be of particular interest in cases of painful bladder syndrome but also for overactive bladder syndrome.

EXAMPLE 2

Effects of Vorapaxar and Atopaxar on a Rat-isolated Bladder Model

The objective of this study was to evaluate the effects of vorapaxar and atopaxar on the amplitude of trypsin- and TFLLR-induced bladder contraction.

These experiments were conducted on naive bladders. The protocol followed was the same as the protocol described in Example 1.

Figure 9:
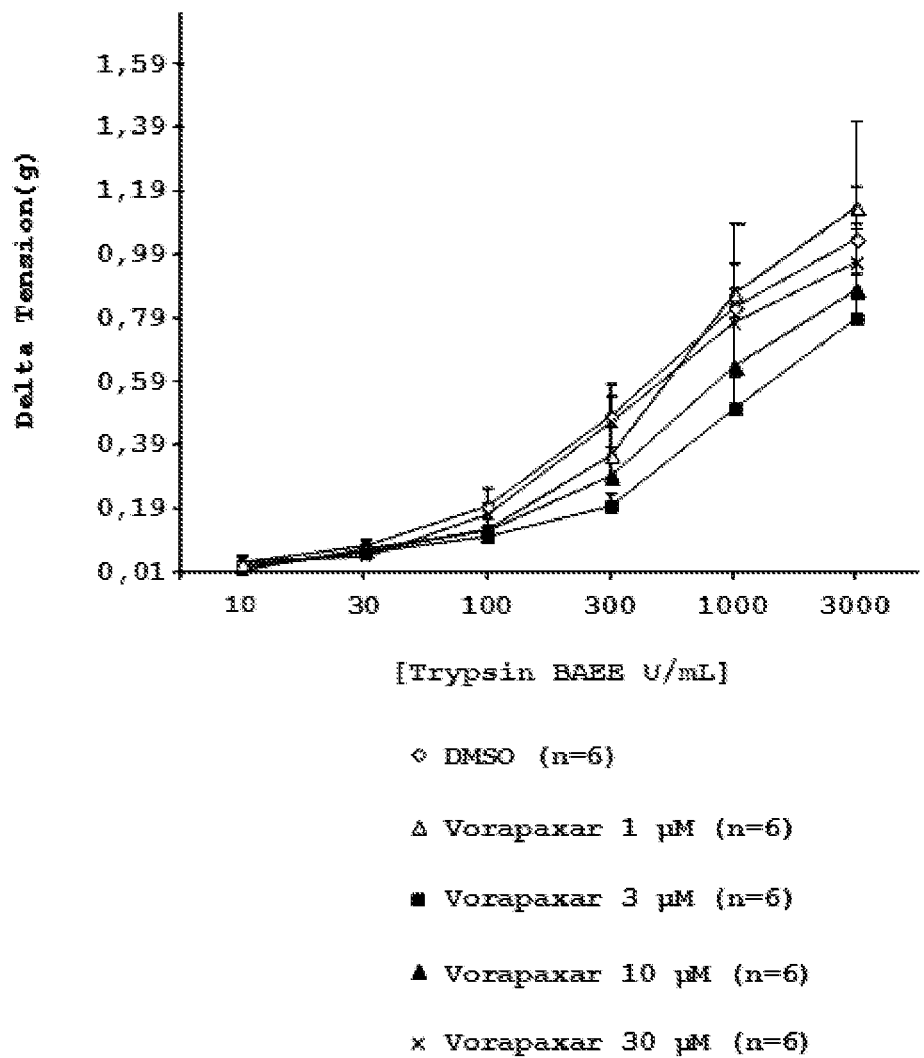
FIG. 9 shows that Vorapaxar antagonizes trypsin-induced bladder contraction in naïve animals.

Results obtained with vorapaxar:

In the presence of trypsin at 3000 BAEE U/mL, inflammation increases bladder contractility by a factor of two. The amplitude of contraction increased from 0.93±0.10 g to 1.97±0.14 g. Vorapaxar at 3 µM antagonises trypsin-induced bladder contraction in naive animals as illustrated in FIG. 9. The amplitude of bladder contraction is antagonised in the presence of 3 µM vorapaxar versus vehicle (0.79±0.14 g versus 1.04±0.16 g, respectively). At a concentration of 10 µM the lesser efficacy is due to the low solubility of the compound. This is confirmed at a concentration of 30 µM.

Figure 10:
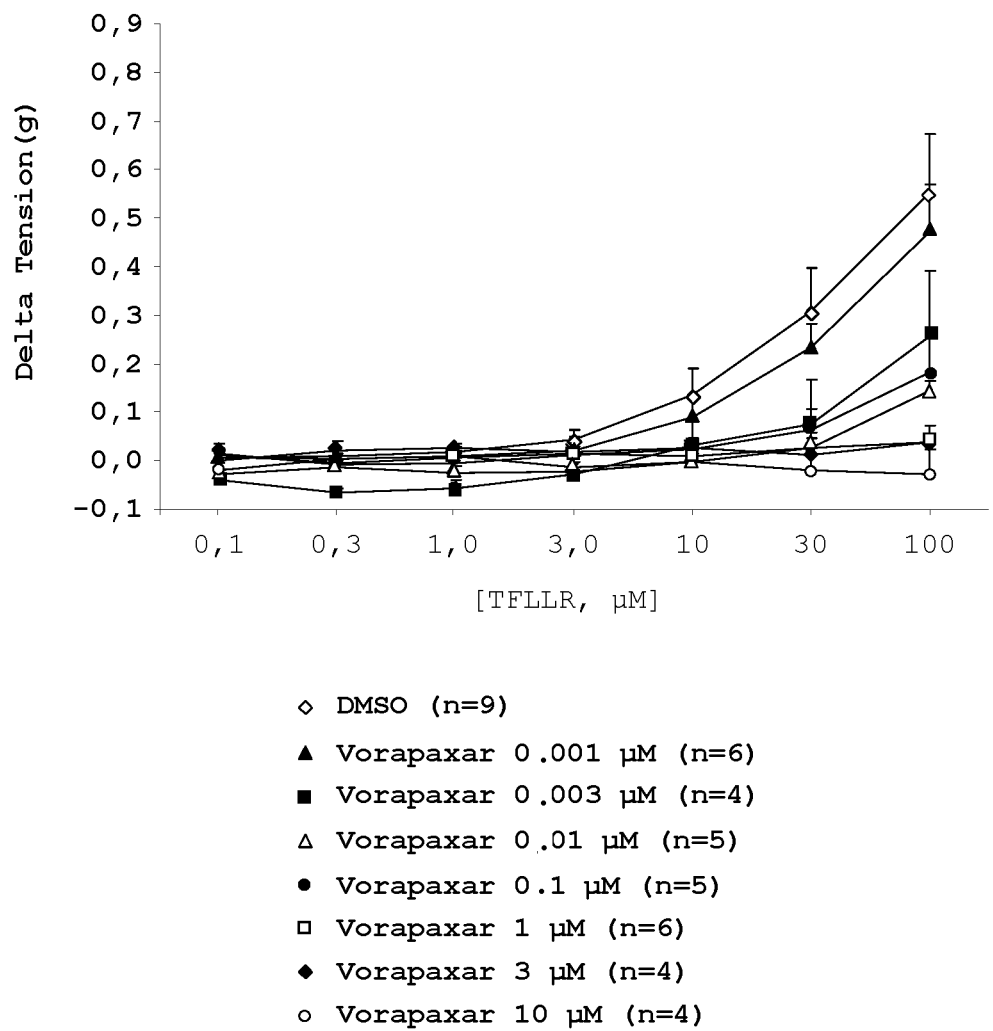
FIG. 10 shows Vorapaxar had concentration-dependent antagonist action on TFLLR-induced bladder contraction in naïve animals.

In the presence of 100 µM TFLLR, bladder contractility increases with PAR1 activation. The amplitude of contraction is 0.57±0.11 g. Vorapaxar has concentration-dependant antagonist action on TFLLR-induced bladder contraction in naive animals (FIG. 10). At 3 nM vorapaxar induces a reduction of nearly 50% in bladder contraction (0.31±0.12 g versus 0.57±0.11 g). At 10 nM vorapaxar reduces bladder contraction by 75% (0.14±0.02 g versus 0.57±0.11 g). From 1 µM, vorapaxar completely abolishes bladder contraction (0.04±0.03 g±0.57±0.11 g), as shown in FIG. 10.

Figure 11:
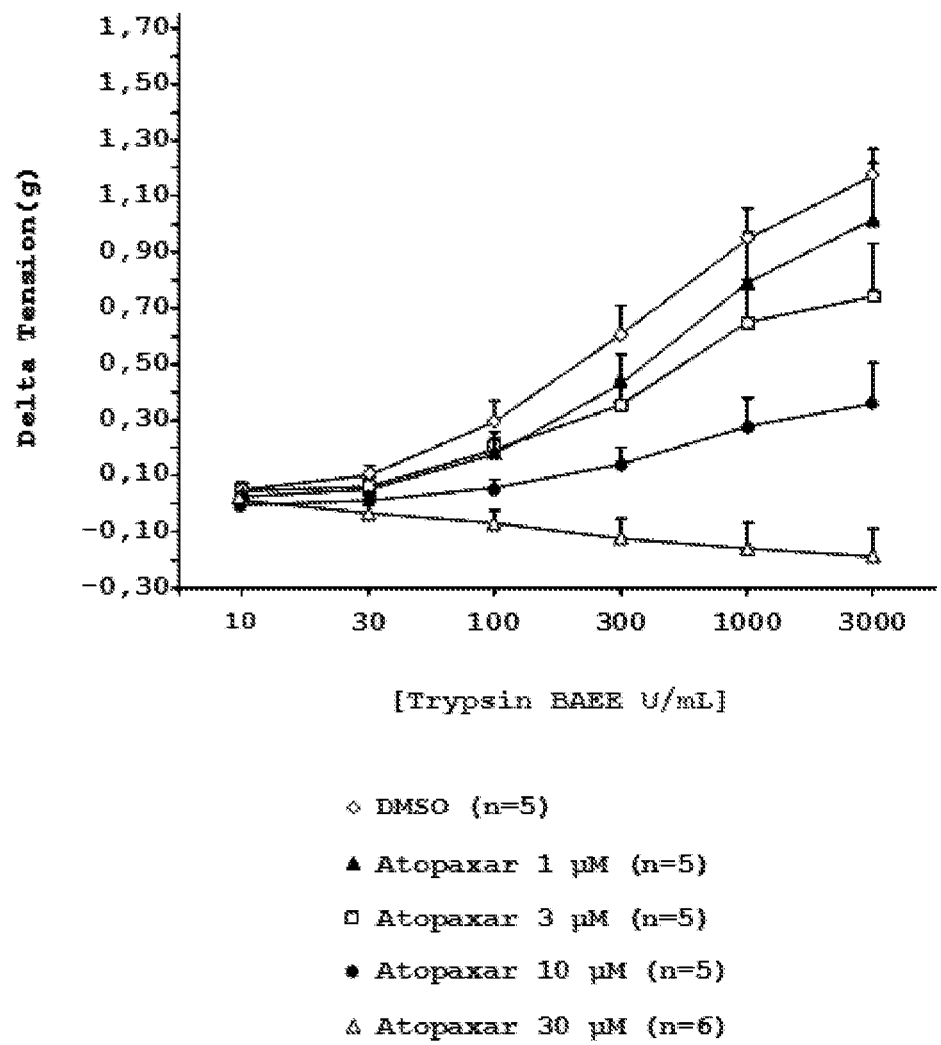
FIG. 11 shows Atopaxar has concentration-dependent antagonist action on trypsin-induced bladder contraction in naïve animals.

Results obtained with atopaxar:

In the presence of 3000 BAEE U/mL trypsin the amplitude of contraction increases by a factor of more than two (0.76±0.08 g versus 1.93±0.09 g). Atopaxar has concentration-dependant antagonist action on trypsin-induced bladder contraction in naive animals as illustrated in FIG. 11. At 1 µM, atopaxar induces a slight reduction in bladder contraction (1.02±0.20 g versus 1.17±0.10 g). At 3 µM, atopaxar causes a 38% reduction in bladder contraction (0.74±0.19 g versus 1.17±0.10 g). At 10 µM atopaxar reduces bladder contraction by 70% (0.36±0.15 g versus 1.17±0.10 g) and completely abolishes contraction at 30 µM (FIG. 11).

Figure 12:
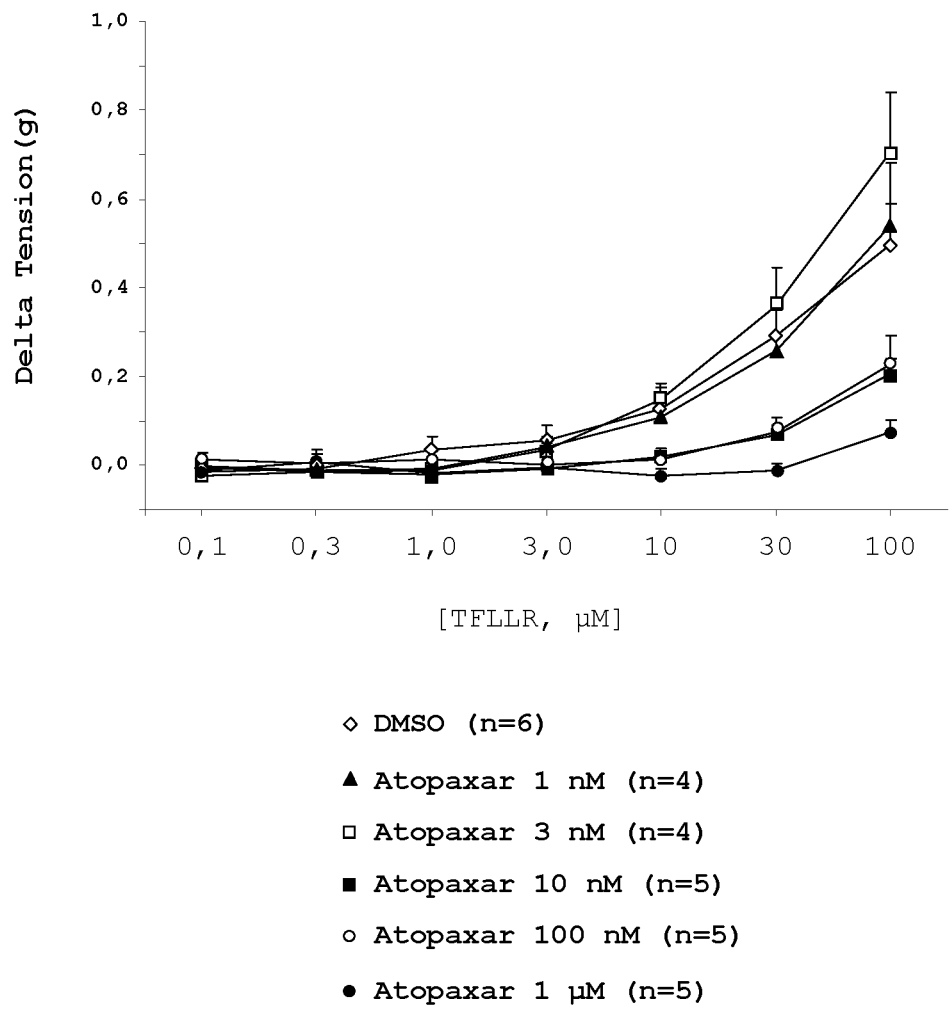
FIG. 12 shows Atopaxar has a concentration-dependent antagonist action on TFLLR-induced bladder contraction in naïve animals.

In the presence of 100 µM TFLLR, bladder contractility is increased with PAR1 activation. The amplitude of contraction reaches 0.50±0.09 g. Atopaxar has concentration-dependant antagonist action on TFLLR-induced bladder contraction in naive animals after 10 nM (FIG. 12). At 10 nM atopaxar induces a reduction in bladder contraction of more than 50% (0.21±0.03 g versus 0.50±0.09 g). At 1 µM atopaxar, bladder contraction is almost completely abolished with a decrease of more than 80% (0.08±0.03 g versus 0.50±0.09 g), as shown in FIG. 12.

To conclude, vorapaxar and atopaxar prevent bladder contractions under physiological conditions. The inventors have therefore shown that PAR1 antagonists efficiently reduce contractile responses i.e. they appear to be of particular interest for pelvi-perineal functional pathologies and in particular in painful bladder syndrome.

The invention claimed is:

1. A method for reducing bladder contractility comprising:
administration to a patient in need thereof of an effective amount of a PAR1 antagonist selected from the group consisting of vorapaxar, atopaxar, 3-(2-Chloro-phenyl)-1-[4-(4-fluoro-benzyl)-piperazin-1-yl]-propanone, and pharmaceutically acceptable salts thereof.

2. The method according to claim 1, wherein the PAR1 antagonist is vorapaxar, atopaxar or one of the pharmaceutically acceptable salts thereof.

3. The method according to claim 1, wherein the PAR1 antagonist is 3-(2-Chloro-phenyl)-1-[4-(4-fluoro-benzyl)-piperazin-1-yl]-propanone or one of the pharmaceutically acceptable salts thereof.

4. A method for reducing bladder contractility in a patient with painful bladder syndrome comprising:
administration to the patient in need thereof of an effective amount of a pharmaceutical composition containing a PAR1 antagonist selected from the group consisting of vorapaxar, atopaxar, 3-(2-Chloro-phenyl)-1-[4-(4-fluoro-benzyl)-piperazin-1-yl]-propanone, and pharmaceutically acceptable salts thereof as active ingredient and at least one pharmaceutically acceptable excipient.

5. The method according to claim 4, wherein the PAR1 antagonist is vorapaxar, atopaxar or one of the pharmaceutically acceptable salts thereof.

6. The method according to claim 4, wherein the PAR1 antagonist is 3-(2-Chloro-phenyl)-1-[4-(4-fluoro-benzyl)-piperazin-1-yl]-propanone or one of the pharmaceutically acceptable salts thereof.

7. The method according to claim 4, wherein the pharmaceutical composition is administered in endovesical administration form.

8. A method for reducing bladder contractility in a patient with overactive bladder syndrome comprising:
administration to the patient in need thereof of an effective amount of a PAR1 antagonist selected from the group consisting of vorapaxar, atopaxar, 3-(2-Chloro-phenyl)-1-[4-(4-fluoro-benzyl)-piperazin-1-yl]-propanone, and pharmaceutically acceptable salts thereof.

9. The method according to claim 8, wherein the PAR1 antagonist is vorapaxar, atopaxar or one of the pharmaceutically acceptable salts thereof.

10. The method according to claim 8, wherein the PAR1 antagonist is 3-(2-Chloro-phenyl)-1-[4-(4-fluoro-benzyl)-piperazin-1-yl]-propanone or one of the pharmaceutically acceptable salts thereof.

11. The method according to claim 1, wherein the patient has painful bladder syndrome.

12. The method according to claim 11, wherein the PAR1 antagonist is administered into the thickness of the bladder wall.

13. The method according to claim 11, wherein the PAR1 antagonist is administered orally.

14. The method according to claim 11, wherein the amount of PAR1 antagonist administered is between 0.1 mg to 1000 mg every 24 hours.

* * * * *